(12) United States Patent
Asai et al.

(10) Patent No.: US 9,381,241 B2
(45) Date of Patent: Jul. 5, 2016

(54) MUCOSAL ADJUVANT COMPOSITION

(75) Inventors: Ken-ichi Asai, Ibaraki (JP); Kazuo Kawakami, Ibaraki (JP); Masami Mochizuki, Ibaraki (JP)

(73) Assignee: KYORITSU SEIYAKU CORPORATION, Ibaraki (JP)

( * ) Notice: Subject to any disclaimer, the term of this patent is extended or adjusted under 35 U.S.C. 154(b) by 0 days.

(21) Appl. No.: 13/876,439

(22) PCT Filed: Sep. 27, 2011

(86) PCT No.: PCT/JP2011/005438
§ 371 (c)(1),
(2), (4) Date: May 3, 2013

(87) PCT Pub. No.: WO2012/042857
PCT Pub. Date: Apr. 5, 2012

(65) Prior Publication Data
US 2013/0302360 A1      Nov. 14, 2013

(30) Foreign Application Priority Data
Sep. 28, 2010  (JP) .................. 2010-216963

(51) Int. Cl.
| A61K 39/00 | (2006.01) |
| A61K 39/39 | (2006.01) |
| A61K 38/16 | (2006.01) |
| C07K 14/235 | (2006.01) |
| A61K 39/12 | (2006.01) |
| A61K 39/02 | (2006.01) |

(52) U.S. Cl.
CPC .............. *A61K 39/39* (2013.01); *A61K 38/162* (2013.01); *A61K 39/099* (2013.01); *A61K 39/12* (2013.01); *C07K 14/235* (2013.01); *A61K 2039/52* (2013.01); *A61K 2039/5252* (2013.01); *A61K 2039/541* (2013.01); *A61K 2039/543* (2013.01); *A61K 2039/55594* (2013.01); *C12N 2710/10034* (2013.01); *C12N 2760/18034* (2013.01)

(58) Field of Classification Search
None
See application file for complete search history.

(56) References Cited

U.S. PATENT DOCUMENTS 7,393,535 B2 *   7/2008  Roberts et al. ............. 424/234.1
2008/0226670 A1 *  9/2008  Dominowski et al. ...... 424/201.1

FOREIGN PATENT DOCUMENTS

| JP | 58-083629 A1 | 5/1983 |
| JP | 59-157029 A1 | 9/1996 |
| JP | 10-36287 A1 | 2/1998 |
| WO | WO95-34322 A1 | 12/1995 |
| WO | WO01-93906 | 12/2001 |
| WO | WO2006-038115 | 4/2006 |
| WO | WO2006-106424 | 10/2006 |

OTHER PUBLICATIONS

Cotter et al. (Infetion and Immunity ,vol. 66, No. 12, pp. 5921-5929, 1998.*
Rajeev, Sreekumari Doctoral Dissertation 2002.*

* cited by examiner

*Primary Examiner* — Ja'Na Hines
*Assistant Examiner* — Khatol Shahnan Shah
(74) *Attorney, Agent, or Firm* — Jeffrey S. Melcher; Manelli Selter PLLC

(57) ABSTRACT

Problem to be Solved: The present invention provides a novel mucosal adjuvant.
Solution: The present invention provides a mucosal adjuvant composition containing at least a composition comprising molecules having a molecular weight in a range of 100 to 300 kDa obtained from cells or culture fluid of *Bordetella bronchiseptica*. Administration of the mucosal adjuvant composition to a non-human animal at a surface of the mucous membrane can enhance immunity at the surface of mucous membrane. Therefore preventive effects against trans-mucosal infection can be increased by administering an inactivated vaccine against trans-mucosal infection and the mucosal adjuvant composition to a non-human animal at a surface of mucous membrane. The present invention is effective for preventing trans-mucosal infections, including one or more infections of e.g., canine parainfluenza, canine adenovirus, canine coronavirus, canine parvovirus, canine distemper virus, canine herpesvirus, reovirus and pneumovirus.

8 Claims, 2 Drawing Sheets

MUCOSAL ADJUVANT COMPOSITION

Relationship to other applications: The present application is a US national phase patent application of PCT/JP2011/005438, filed 27 Sep. 2011 (published as WO/2012/042857) and claims the benefit of, and priority to, Japanese patent application JP2010-216963, filed 28 Sep. 2010. Both of these applications are hereby incorporated by reference to the fullest extent allowed by law.

Incorporation by reference: All documents and publications filed in connection with this application and mentioned in this and any priority application, including but not limited to WO95/34322, WO2006/106424, WO2006/38115, Japanese Patent Laid-Open No. S58-83629, Japanese Patent Laid-Open No. S59-157029, are hereby incorporated by reference to the fullest extent allowed by law.

FIELD OF INVENTION

The present invention relates to a mucosal adjuvant composition containing at least a composition comprising molecules having a molecular weight in a range of 100 to 300 kDa obtained from cells or culture fluid of *Bordetella bronchiseptica*, and to a use thereof. The present invention also relates to a vaccine formulation for preventing trans-mucosal infection comprising the mucosal adjuvant composition, a method of preventing trans-mucosal infection in a non-human animal, a method of manufacturing the mucosal adjuvant composition and the like.

BACKGROUND

Vaccines are widely used for preventing diseases such as infectious diseases. A vaccine is a biological formulation comprising an antigen which produces an immune response in a living organism. It prevents infection by a specific disease agent by inoculation with an inactivated or attenuated antigen into an animal such as human so as to induce immunity against a specific disease.

Vaccines can be broadly grouped as: live vaccines, inactivated vaccines, a toxoids and the like. A live vaccine refers to an attenuated vaccine produced by attenuating toxicity and virulence of a pathogen. The vaccine can multiply in the body of an inoculated animal. An inactivated vaccine refers to a vaccine prepared from a pathogen treated with formalin, ultraviolet radiation and the like to abolish its infectivity, toxicity and virulence, or from a component thereof. The vaccine will not multiply in the body of an inoculated animal. A toxoid is a class of inactivated vaccines, which is prepared by removing toxins from bacterium to abolish its toxicity and leaving only its immunogenicity intact.

In general, live vaccines can induce a good immune response in many cases while they have higher risks of toxicity than inactivated vaccines. In contrast, inactivated vaccines and the like are safer than live vaccines while immunogenicity of inactivated vaccines is often too weak to achieve sufficient immune effects by single administration. Therefore, inactivated vaccines may be administered in repeated doses or in combination with an adjuvant to achieve sufficient immune effects.

An adjuvant refers to a substance which enhances an immune response against an antigen by administering it in combination with that antigen to a living organism. By adding an adjuvant to an inactivated vaccine and the like, immune effects can be enhanced and duration of effective immunity can be extended. The dose and frequency of administration of a vaccine can be reduced, which in turn results in decreasing its production volume.

Best known adjuvants include Complete Freund's adjuvant and Incomplete Freund's adjuvant. Complete Freund's adjuvant is a mixture of liquid paraffin, surfactant and cells of *Tubercle Bacillus* while Incomplete Freund's adjuvant is a mixture of liquid paraffin and surfactant. These adjuvants are commonly used for laboratory animals, but they are used neither for human nor for animals because they show a strong local response at a site of inoculation. In addition, precipitated adjuvants such as aluminium hydroxide (alum) and sodium hydroxide, oily adjuvants such as liquid paraffin, sterilized microorganism and the like are known. Note that only an aluminium hydroxide gel is currently approved for human use.

In the case of trans-mucosal infections such as respiratory infection, vaccination via injection often fails to effectively induce immunity at a site of infection (a surface of mucous membrane). In contrast, a mucosal vaccine attracts attention as a means for reliably and efficiently raising an immune response at a surface of mucous membrane. A mucosal vaccine is a vaccine in which an antigen is directly administered to a surface of mucous membrane in order to activate an immune system present at a surface of mucous membrane.

In the immune system of the mucous membrane, not only are the responses due to IgG antibody of the systemic immune system but also to secretory IgA antibody, cytotoxic T-cells, delayed allergic reaction mediated Th1 cells and the like, which are involved in the defense mechanism. Among these, it is suggested that secretory IgA functions to neutralize a pathogen by secretion at the mucous membrane, and plays a significant role in resistance against a pathogen of trans-mucosal infection. Therefore, a mucosal vaccine is expected to achieve more effective immune effect against trans-mucosal infection than a common injectable vaccine.

However, in the case of a mucosal vaccine, administration of an antigen alone to mucous membrane often cannot induce sufficient immunity since a surface of mucous membrane is always exposed to invasion of foreign objects. Therefore, a mucosal vaccine should be used in combination with a highly efficacious adjuvant for mucosal immunity (a mucosal adjuvant). In human beings, cholera toxins, *E. coli* heat-labile toxins and the like have been tried as mucosal adjuvants.

Trans-mucosal infections in canine include, for example, canine infectious tracheobronchitis (Kennel Cough), canine distemper, canine parvovirus infection, canine coronavirus infection and canine herpesvirus infection. The canine infectious tracheobronchitis is a disease showing dry cough, nasal discharge, fever and the like as main symptoms. Its main pathogens include canine adenovirus type 2, canine parainfluenza virus and *Bordetella bronchiseptica* (scientific name "*Bordetella bronchiseptica*," hereinafter), and in addition, canine adenovirus type 1, canine herpesvirus, reovirus, pneumovirus and the like also cause this disease.

Trans-mucosal infections in feline include, for example, feline infectious tracheobronchitis, feline panleukopenia, feline infectious peritonitis/feline intestinal coronavirus infection, feline leukemia, feline immunodeficiency virus infection. Feline infectious tracheobronchitis is a disease showing fever, nasal discharge, sneezing and the like as main symptoms. Its main pathogens are feline calicivirus and feline herpesvirus, and in addition, *Chlamydophila felis* (scientific name "*Chlamydophila felis*," hereinafter), *Bordetella bronchiseptica* and the like also cause this disease.

In addition, there are various trans-mucosal infections in mink, rat, guinea pig, rabbit, ferret, mouse and the like.

For vaccines against canine respiratory infection, for example, live or inactivated vaccines of canine parvovirus, mixed live or inactivated vaccines of canine distemper, canine adenovirus, canine parainfluenza virus, canine coronavirus and the like have been used, respectively. Further, for vaccines against feline respiratory infection, for example, mixed live vaccines of feline viral rhinotracheitis, feline calicivirus, feline panleukopenia, aluminium-gel-adjuvant-added inactivated vaccines, oily-adjuvant-added inactivated vaccines and the like have been used.

*Bordetella bronchiseptica*, which is a gram-negative obligate aerobic *bacillus*, is a pathogenic bacterium of swine atrophic rhinitis and *Bordetella bronchiseptica* disease in rat, guinea pig, rabbit, ferret, feline, canine, swine, monkey and the like. As described above, it is also one of the pathogenic bacteria of canine infectious tracheobronchitis and feline infectious tracheobronchitis. Note that other *Bordetella* bacteria include *Bordetella pertussis* (scientific name "*Bordetella pertussis*") and a pathogenic bacterium of *Meleagris gallopavo coryza* (scientific name "*Bordetella avium*").

For vaccines against swine atrophic rhinitis, for example, inactivated vaccines of swine *Bordetella* infection, purified inactivated vaccines, oily-adjuvant-added mixed inactivated vaccines with swine pasteurellosis, mixed toxoids with *Pasteurella multocida* and the like have been used.

For example, Patent Document 1 (see below) describes a mixed toxoid which is effective for preventing swine atrophic rhinitis, the toxoid comprising a necrotoxic toxoid produced by *Bordetella* and toxinogenic *Pasteurella* as a main ingredient.

Patent Document 2 describes a vaccine composition against Kennel Cough comprising *Bordetella bronchiseptica* p68 antigen. Patent Document 3 describes a canine polyvalent vaccine against Kennel Cough comprising one or more of canine distemper virus, canine adenovirus type 2, canine parainfluenza virus, canine coronavirus, canine parvovirus and leptospire; and *Bordetella bronchiseptica* p68 antigen. Patent Document 4 and 5 describe an immunoadjuvant comprising cells and cell components of *Bordetella bronchiseptica* from swine.

Patent Document 1: WO95/34322
Patent Document 2: WO2006/106424
Patent Document 3: WO2006/38115
Patent Document 4: Japanese Patent Laid-Open No. S58-83629
Patent Document 5: Japanese Patent Laid-Open No. S59-157029

DISCLOSURE OF THE INVENTION

Problem to be Solved by the Invention

An object of the present invention is to provide a novel mucosal adjuvant for a vaccine against trans-mucosal infections and the like.

Means for Solving the Problem

The present inventors have newly found that a composition comprising molecules having a molecular weight in a range of 100 to 300 kDa obtained from cells or culture fluid of *Bordetella bronchiseptica* effectively enhances an immunoreaction at a surface of the mucous membrane induced by a vaccine against trans-mucosal infection and the like.

Accordingly, the present invention provides a mucosal adjuvant composition containing at least molecules having a molecular weight in a range of 100 to 300 kDa obtained from cells or culture fluid of *Bordetella bronchiseptica*

Administration of the mucosal adjuvant composition to a non-human animal and the like at a surface of mucous membrane can potentiate immunity at the surface of mucous membrane. Therefore, for example, preventive effects against trans-mucosal infection can be increased by administering a vaccine against trans-mucosal infection and the presently disclosed mucosal adjuvant composition to a non-human animal.

As described above, there is a problem that sufficient immunity may often not be induced when an antigen alone is administered at the mucous membrane, although more effective immune effects against trans-mucosal infection could be obtained compared with those by a usual injectable vaccine because a mucosal vaccine induces not only a response by IgG antibody, but also an immune response by secretory IgA antibody and the like. In contrast, according to the present invention, by combining this mucosal adjuvant composition with a vaccine having poor effects for preventing diseases when administered alone at mucous membrane, those diseases were able to be effectively prevented. Therefore, the present invention advantageously allows such a vaccine to be used as a mucosal vaccine.

Further, as a result, because, for example, an inactivated vaccine can be used for effective mucosal immunization, a risk such as toxicity reversion can be avoided and higher safety can be achieved as compared to the case where an attenuated live vaccine is administered. In addition, immunological enhancement effects according to the present invention can decrease a dosage amount of vaccine itself to reduce manufacturing cost, sales cost and the like.

Effects of the Invention

The present invention can potentiate immunity at a surface of mucous membrane. Therefore, for example, it is effective as a mucosal adjuvant for a vaccine against trans-mucosal infection and the like.

BEST MODES FOR CARRYING OUT THE INVENTION

A Mucosal Adjuvant Composition According to the Present Invention, and a Method for Manufacturing the Same.

The present invention involves a composition comprising molecules having a molecular weight in a range of 30 to 500 kDa obtained from cells or culture fluid of *Bordetella bronchiseptica*, and encompasses all mucosal adjuvant compositions comprising at least a substance having a mucosal adjuvant activity.

A method of manufacturing a mucosal adjuvant composition according to the present invention has no particular limitation. The present mucosal adjuvant composition can be obtained by, for example, culturing *Bordetella bronchiseptica*, and purifying a composition in the range of 30 to 500 kDa from its culture supernatant using ultrafiltration and the like.

There is no particular limitation for *Bordetella bronchiseptica* strains. For example, the KR001-A01 strain (depository facility: The National Institute of Advanced Industrial Science and Technology, International Patent Organism Depositary; location: Tsukuba Center Central 6, 1-1-1, Higashi, Tsukuba City, Ibaraki Prefecture, Japan, Accession Number FERM BP-11415, deposition date: Jul. 9, 2010, the strain was collected in Japan) can be preferably used.

For a method of culturing *Bordetella bronchiseptica*, any known culturing methods using liquid medium can be utilized.

For example, Bordetella bronchiseptica is cultured for 1 to 7 days at 30 to 40° C. (preferably at 37° C.) using known culture medium for growth of *Bordetella bronchiseptica*, and then a culture supernatant is obtained by, for example, centrifuging and filtering the culture. The culture supernatant is purified through, for example, an ultrafiltration filter having a molecular cutoff of 30 to 500 kDa to obtain a stock solution of a mucosal adjuvant composition.

The concentration of proteins in this stock solution is preferably 0.05 to 5.0 mg/mL. In addition, a value of HA is preferably 16 to 2,048 times.

This stock solution is appropriately diluted and prepared to give an adjuvant for use. Dilution factors of this mucosal adjuvant composition have no particular limitation. For example, it is diluted to give a dosage amount per dose per animal of 1 to 500 μg (preferably 12 to 160 μg) in protein weight and 1 to 400 units (preferably 8 to 120 units) in a unit of HA.

The mucosal adjuvant composition according to the present invention is a mixture of multiple components having a molecular weight in a range of 30 to 500 kDa, and the mixture contains HA (haemagglutinin or erythrocyte agglutinin, about 180 kDa, the same hereinafter). HA is presumably one of the active ingredients for adjuvant effects. Therefore, the present mucosal adjuvant composition is preferred to contain HA as a main active ingredient. That is, the molecular weight is preferably in the range of 100 to 300 kDa, and more preferably 150 to 220 kDa. When purifying only HA, any known purification means can be used.

In addition, depending on purpose, use and the like, buffer, isotonizing agent, soothing agent, preservative agent, antioxidant and the like may be appropriately added to the present mucosal adjuvant composition.

Preferred examples of buffer can include, for example, buffer solutions such as phosphate, acetate, carbonate and citrate.

Preferred examples for isotonizing agents can include, for example, sodium chloride, glycerol and D-mannitol.

Preferred examples for soothing agents can include, for example, benzyl alcohol.

Preferred examples for preservative agents can include, for example, thimerosal, p-hydroxybenzoate esters, phenoxyethanol, chlorobutanol, benzyl alcohol, phenethyl alcohol, dehydroacetic acid and sorbic acid.

Preferred examples for anti-oxidants can include, for example, sulfite and ascorbic acid.

In addition, this medicament may contain an auxiliary ingredient such as, for example, light absorbing dyes for assisting preservation and effects (riboflavin, adenine, adenosine and the like), chelating agents and reducing agents for stabilization (vitamin C, citric acid and the like) and carbohydrates (sorbitol, lactose, mannitol, starch, sucrose, glucose, dextran and the like), casein digests and various vitamins.

Depending on purpose, use and the like, other known adjuvants also may be appropriately added to the present mucosal adjuvant composition.

Adjuvants to be added include, for example, precipitated adjuvants such as aluminium hydroxide (alum) and sodium hydroxide; oily adjuvants such as liquid paraffin; sterilized microorganisms such as cholera toxins and *E. coli* heat-labile toxins.

Note that the present invention also encompasses any methods of manufacturing a mucosal adjuvant composition, comprising at least use of the aforementioned composition in manufacturing a mucosal adjuvant composition and a step of preparing the composition.

Vaccine Formulation and the Like for Preventing Trans-Mucosal Infection According to the Present Invention The mucosal vaccine formulation for preventing trans-mucosal infection according to the present invention encompasses any formulation comprising at least a vaccine against trans-mucosal infection and the above-mentioned mucosal adjuvant composition.

There is no particular limitation for vaccines long as they are against trans-mucosal infection. For example, a live vaccine, an inactivated vaccine, a toxoid and the like can be used in combination with the above-mentioned mucosal adjuvant composition. From the viewpoint of safety, the ability of the present invention to increase immune effects and the like, an inactivated vaccine is preferred. Further, the vaccine may be against a single disease, or it may be a mixed vaccine against two or more diseases.

Since the adjuvant composition according to the present invention potentiates immune effects in particular at a surface of mucous membrane, a vaccine which can be administered via a trans-mucosal route (a mucosal vaccine) is preferred. When safety issues as described above are further taken into account, an inactivated mucosal vaccine is most preferred. However, since immune effects can be enhanced by using the mucosal adjuvant composition according to the present invention, for example, even a vaccine conventionally showing insufficient immune effects by trans-mucosal administration could produce sufficient immune effects if used in combination with the present mucosal adjuvant composition. Therefore, "a mucosal vaccine" in the present invention encompasses any vaccines which can be administered at a surface of mucous membrane. Further, it encompass a wide range of vaccines which become effective only when used in combination with the mucosal adjuvant composition (the same hereinafter).

In addition, by the combination of a vaccine and the mucosal adjuvant composition, duration of immunity can be extended and a dose and frequency of administration of a vaccine can be reduced, resulting in a decreased production volume of the vaccine.

A dosage form of the vaccine formulation can be any known dosage form without any particular limitation. For example, it may be used as a liquid formulation containing a vaccine and a mucosal adjuvant composition or as a pellet formulation which is formed, for example, by lyophilizing both the vaccine and the composition, and then dissolved in purified water and the like prior to use. In addition, depending on purpose, use etc., buffer, isotonizing agent, soothing agent, preservative agent, anti-oxidant and the like may be appropriately added as described above.

A Method of Preventing Trans-Mucosal Infection According to the Present Invention.

In one example, trans-mucosal infection in a non-human animal can be effectively prevented by administering a single or mixed vaccine against trans-mucosal infection together with the aforementioned mucosal adjuvant composition, simultaneously or separately.

For a vaccine and a mucosal adjuvant composition, the same materials as described above can be used. Further, depending on species, age, weight and the like of an animal, the timing, mode etc. of administration of a vaccine and a mucosal adjuvant composition can be appropriately selected without any particular limitation.

For example, a vaccine formulation for preventing trans-mucosal infection containing at least a vaccine against the trans-mucosal infection and the above-mentioned mucosal adjuvant composition may be administered to an animal at a surface of mucous membrane for immunization once, or two or more times with a 1 to 60 day interval.

Further, a mucosal adjuvant composition may be administered to an animal at a surface of a mucous membrane once or multiple times to enhance immunity at the surface of mucous membrane 1 to 30 days before the administration of a vaccine, and then the vaccine can be administered once or multiple times for immunization.

When a vaccine and a mucosal adjuvant composition are administered separately, the modes of administration of the vaccine can be appropriately selected from intravenous injection, subcutaneous injection, intramuscular injection, trans-mucosal administration and the like, depending on purposes and types, but not limited to trans-mucosal administration only. Nonetheless, a vaccine that can be administered via a trans-mucosal route (a mucosal vaccine) appears to be most preferred because the mucosal adjuvant composition according to the present invention can potentiate immune effects in particular at a surface of mucous membrane.

Administration at a surface of a mucous membrane can be performed by any known methods. For example, in the case of administration via nasal mucosa, it may be directly applied to a surface of mucous membrane in the nasal cavity using a dropper or a syringe, or may be sprayed to a surface of a mucous membrane in the nasal cavity. Similar modes of administration apply for a surface of other mucous membranes.

A dose of vaccine will be appropriately determined depending on the vaccine and the mucosal adjuvant composition used in the combination with it. For example, a dose of a common vaccine having $10^6$ to $10^9$ $TCID_{50}$/mL of virus may be administered in an amount of 0.05 to 3.0 mL.

For a dose of a mucosal adjuvant composition, a dosage amount per dose per animal can be, for example, 1 to 500 µg in protein weight (preferably 12 to 160 µg), 1 to 400 units in a unit of HA (preferably 8 to 120 units). When administered to a dog in the nasal cavity, for example, a dose of 0.05 to 3.0 mL (preferably 0.2 to 1.0 mL) is appropriate for a surface of mucous membrane. It can be appropriately determined for other animals, considering the size of the animal etc.

The present invention may be applicable to any non-human animals without any particular limitations. For example, the present invention may be applicable for preventing infectious diseases in, for example canine, feline, mink, rat, guinea pig, rabbit, ferret and mouse. Canine and feline are preferred.

Any diseases may be indicated without any particular limitations as long as they are infectious diseases which invade via the mucous membrane. Invasion pathways of pathogenic microorganism through mucous membrane include, for example, transnasal/transtracheal, oral and transurogenital. Note that the mucosal adjuvant composition according to the present invention is most preferably used in combination with a vaccine against pathogenic microorganism which transnasally/transtracheally invades.

Trans-mucosal infections in canine include, for example, canine infectious tracheobronchitis (Kennel Cough), canine distemper, canine parvovirus infection, canine coronavirus infection and canine herpesvirus infection. Major pathogens for canine infectious tracheobronchitis include canine adenovirus type 2, canine parainfluenza virus and *Bordetella bronchiseptica*. In addition, canine adenovirus type 1, canine herpesvirus, reovirus, pneumovirus and the like can be a pathogen.

The present invention is most preferably indicated for canine trans-mucosal infections comprising at least one or more infections of canine parainfluenza virus, canine adenovirus, canine coronavirus, canine parvovirus, canine distemper virus, canine herpesvirus, reovirus and pneumovirus.

Trans-mucosal infections in feline include, for example, feline infectious tracheobronchitis, feline panleukopenia, feline infectious peritonitis/feline intestinal coronavirus infection, feline leukemia and feline immunodeficiency virus infection. Pathogens for feline infectious tracheobronchitis can include feline calicivirus, feline herpesvirus. In addition, *Chlamydophila felis* and *Bordetella bronchiseptica* can be a pathogen.

Trans-mucosal infections in mink include, for example, Aleutian mink disease and mink viral enteritis.

Trans-mucosal infections in rat include, for example, Sendai virus infection, sialadenitis and dacryoadenitis, parvovirus infection, *Pneumococci* infection and pasteurellosis. Trans-mucosal infections in guinea pig include, for example, pasteurellosis and *Streptococcal* infection. Trans-mucosal infections in rabbit include, for example, Sendai virus infection and pasteurellosis. In addition, there are also various trans-mucosal infections in ferret, mouse and the like.

EXAMPLE 1

In Example 1, a mucosal adjuvant composition according to the present invention was prepared.

*Bordetella bronchiseptica* KR001-A01 strain (Accession Number FERM P-21984, the same hereinafter) was cultured for 3 days at 37° C. For growth medium, a known liquid growth medium for *Bordetella bronchisepticas* was used.

The culture medium was centrifuged (16,000×g for 30 minutes at 4° C.) to obtain a culture supernatant. Then supernatant was purified through an ultrafiltration filter with a molecular cutoff of 30 to 500 kDa to obtain a stock solution of a mucosal adjuvant composition.

The protein concentration and the HA value of the stock solution was 1.2 mg/mL and 256 times, respectively.

The stock solution was subjected to 4 to 20% SDS-PAGE (polyacrylamide gel electrophoresis, the same hereinafter).

The results are shown in FIG. 1. FIG. 1 shows a photograph representing the results from SDS-PAGE of the mucosal adjuvant composition. In FIG. 1, Lane 1 and Lane 4 correspond to molecular weight markers. Lane 2 and Lane 3 correspond to the results from electrophoresis of the culture supernatant and the stock solution of the mucosal adjuvant composition obtained, respectively. Each number in FIG. 1 represents a molecular weight (unit: kDa).

As shown in FIG. 1, a band was observed around 180 kDa (see the arrow in the figure) when the stock solution of the mucosal adjuvant composition was electrophoresed (Lane 3). This band appears to come from HA.

EXAMPLE 2

In Example 2, a canine parainfluenza virus inactivated vaccine and an adjuvant according to the present invention were administered to a dog at the nasal mucosa to investigate preventive effects against the disease.

For a test vaccine, an inactivated antigen from canine parainfluenza virus (a titer before inactivation: $10^{7.5}$, $TCID_{50}$) was used. For an adjuvant, the mucosal adjuvant composition prepared in Example 1 was used.

The mixture of the adjuvant and the vaccine was intranasally administered in an amount of 0.6 mL to each beagle dog (n=3) negative to canine parainfluenza virus antibody. Two weeks after that, an additional dose was similarly administered. One week after that, a virus solution ($10^{8.6}$, $TCID_{50}$/ mL) of the canine parainfluenza virus challenge strain was then administered in an amount of 0.6 mL to each subject at the nasal cavity to infect it with canine parainfluenza virus. Swab from the nasal cavity was taken from each of the subjects on Days 3, 5, 6 and 7 after the administration of the canine parainfluenza virus challenge strain.

A solution of the nasal cavity swab was inoculated to MDCK cells and cultured, and then virus infection was determined by a hemagglutination reaction against guinea pig hemocyte, and a virus titer was measured.

The results are shown in FIG. 2. FIG. 2 shows a graph which illustrates infection inhibition effects of canine parainfluenza virus when the canine parainfluenza virus inactivated vaccine and the adjuvant prepared in Example 1 were administered. In the graph of FIG. 2, the vertical axis and the horizontal axis represent a virus titer (unit: $Log_{10}TCID_{50}$) and the number of days after the challenge (infection) with the canine parainfluenza virus, respectively. The three bars in the graph represent, from the left, a virus titer in a group where the canine parainfluenza virus inactivated vaccine and the adjuvant prepared in Example 1 were administered (CPIV+Bb), a virus titer in a group where the canine parainfluenza virus inactivated vaccine alone was administered in the same amount (CPIV, n=3) and a virus titer in a non-administered group (control, n=3), respectively.

As shown in FIG. 2, when the canine parainfluenza virus inactivated vaccine and the adjuvant prepared in Example 1 were administered, the virus titer was decreased on Day 5 after the challenge with the canine parainfluenza virus, and the titer was almost 0 on Day 6 after the challenge, showing a contrast to the case where the canine parainfluenza virus inactivated vaccine alone was administered. On the other hand, when the canine parainfluenza virus inactivated vaccine alone was administered, virtually no significant difference was observed compared to the non-administered group (the control group), showing that almost no immune effect against the canine parainfluenza was observed.

These results indicate that the mucosal administration of the mixture of the canine parainfluenza virus inactivated vaccine and the adjuvant according to the present invention raises significant immune effects, and i.e., that the mucosal adjuvant composition according to the present invention has significant immunological enhancement effects in particular as a mucosal adjuvant.

Note that given the results from Example 1 and this Example, HA, which is contained in a large amount in the mucosal adjuvant composition, appears to be one of the main active ingredients for the adjuvant effects. Therefore, the present mucosal adjuvant composition is preferred to contain HA as a main active ingredient. That is, the mucosal adjuvant composition preferably comprises molecules having a molecular weight in a range of 100 to 300 kDa, more preferably a molecular weight in a range of 150 to 220 kDa (the same hereinafter).

EXAMPLE 3

In Example 3, a canine adenovirus inactivated vaccine and an adjuvant according to the present invention were administered to a dog at the nasal mucosa to investigate preventive effects against the disease.

For a test vaccine, an inactivated antigen from canine adenovirus type 2 (a titer before inactivation: $10^{8.4}$, $TCID_{50}$) was used. For an adjuvant, the mucosal adjuvant composition prepared in Example 1 was used.

The mixture of the adjuvant and the vaccine was intranasally administered in an amount of 0.6 mL to each beagle dog (n=3) negative to canine adenovirus antibody. Two weeks after that, an additional dose was similarly administered. One week after that, a virus solution ($10^{8.5}$, $TCID_{50}$/mL) of the canine adenovirus type 2 challenge strain was then administered in an amount of 0.25 mL to each subject at the nasal cavity to infect it with canine adenovirus type 2. Swab from the nasal cavity was taken from each of the subjects on Days 3, 4, 5, and 6 after the administration of the canine adenovirus type 2 challenge strain.

A solution of the nasal cavity swab was inoculated to MDCK cells and cultured, and then virus infection was determined by the cytopathic effect (CPE), and a virus titer was measured.

The results are shown in FIG. 3. FIG. 3 shows the graph which illustrates infection inhibiting effects of canine adenovirus type 2 infection when the canine adenovirus type 2 inactivated vaccine and the adjuvant prepared in Example 1 were administered. In the graph of FIG. 3, the vertical axis and the horizontal axis represent a virus titer (unit: $Log_{10}TCID_{50}$) and the number of days after the challenge (infection) with the canine adenovirus, respectively. The three bars in the graph represent, from the left, a virus titer in a group where the canine adenovirus inactivated vaccine and the adjuvant according to the present invention were administered (CAV+Bb), a virus titer in a group where the canine adenovirus inactivated vaccine alone was administered in the same amount (CAV, n=3) and a virus titer in a non-administered group (control, n=3), respectively.

As shown in FIG. 3, when the canine adenovirus type 2 inactivated vaccine and the adjuvant prepared in Example 1 were administered, the virus titer was significantly decreased from Day 4 after the challenge with the canine adenovirus type 2, showing a contrast to the case where the canine adenovirus type 2 inactivated vaccine alone was administered. On the other hand, when the canine adenovirus type 2 inactivated vaccine alone was administered, no significant difference was observed as compared to the non-administered group (the non-treated group) except for on Day 6.

These results indicate that the mucosal administration of the mixture of the canine adenovirus type 2 inactivated vaccine and the adjuvant according to the present invention raises significant immune effects, and i.e., that the mucosal adjuvant composition according to the present invention has significant immunological enhancement effects in particular as a mucosal adjuvant as in Example 2.

As described above, in vaccinating an animal and the like with a mucosal vaccine against respiratory diseases, the mucosal adjuvant composition prepared in Example 1 produces significant immunological enhancement effects when used as an adjuvant. Further, this mucosal adjuvant composition is also effective for a vaccine formulation against mixed respiratory infections such as canine infectious tracheobronchitis because it produces adjuvant effects for a plural of vaccines against respiratory diseases.

EXAMPLE 4

In Example 4, the effects of *Bordetella bronchiseptica* as a vaccine were investigated.

For a test vaccine, a diluted solution was used in which the stock solution of the adjuvant composition prepared in Example 1 was diluted with PBS (phosphate buffer, the same hereinafter). The concentration of the test vaccine was adjusted to give 16 units of HA in 0.5 mL.

For a test dog, four 4-week old beagle dogs negative to *Bordetella* hemagglutination inhibition antibody were used.

The test dogs were kept in isolators and fed with commercial dry food and with ad libitum water supply.

To the test dogs (n=2), 0.5 mL of the vaccine was intranasally administered, and an additional dose was given similarly two weeks after that. One week after that, a 1 mL bacterial suspension of Bordetella bronchiseptica KR001-A01 strain was then administered as a challenge strain to each subject in the nasal cavity to infect it with Bordetella bronchiseptica. Viable cell counts of this strain were $1 \times 10^9$ CFU/mL as measured with Bordet-Gengou's medium. Note that for the control group (n=2), alternatively, 0.5 mL PBS was transnasally administered for vaccination.

After the challenge with Bordetella bronchiseptica, general clinical observation was performed for each dog for 21 days, and its clinical symptoms were scored. The clinical scores were computed by scoring symptoms according to the following criteria every day during the observation period and adding them together. (1) Three points when body temperature (rectal temperature) is 40.0° C. or more, two points when 39.6 to 39.9° C., one point when 39.2 to 39.5° C.; (2) one point when hypodynamia is observed; (3) two points when serious anorexia is observed, one point when mild anorexia is observed; (4) one point when diarrhea is observed; (5) one point when vomiting is observed; (6) one point when dehydration is observed; (7) one point when lacrimation or eye discharge is observed in the eye; (8) three points when serious purulent nasal discharge is observed, two points when mild purulent nasal discharge is observed, one point when water-like nasal discharge is observed; (9) three points when serious frequent coughing is observed, two points when mild frequent coughing is observed, one point when occasional coughing is observed; (10) two points when frequent sneezing occurs, one point when occasional sneezing is observed; (11) one point when abnormal respiratory sound is observed; (12) 100 points upon death.

The results show that in the control group, abnormal findings such as coughing, nasal discharge, eye discharge and the like were observed nearly every day during the observation period after the challenge with Bordetella bronchiseptica whereas any clinical abnormalities were not observed except for transient diarrhea and slight increase in body temperature in the vaccine treated group. Further, in the vaccine treated group, almost no symptom of upper respiratory infection, which is characteristic of canine infectious tracheobronchitis, was observed. The total clinical scores were 41 points and 51 points (the mean value in the group was 46 points) in the control group, and 4 points and 3 points (the mean value in the group was 3.5 points) in the vaccine treated group, respectively.

As described above, when the adjuvant composition prepared in Example 1 as a vaccine was transnasally administered twice, the development of symptoms of upper respiratory infection due to Bordetella bronchiseptica was able to be prevented in spite of a small dose of 16 units of HA. The results show that, in addition to the mucosal adjuvant composition prepared in Example 1 being effective as a mucosal adjuvant for a vaccine against trans-mucosal infection, it is also effective as a mucosal vaccine against Bordetella bronchiseptica infection.

For example, in addition to various viruses and the like, Bordetella bronchiseptica itself also will be a pathogen of trans-mucosal infection in canine and feline, as described above. In particular, as described above, in addition to canine adenovirus type 2 and canine parainfluenza virus, Bordetella bronchiseptica itself is one of the main pathogens for canine infectious tracheobronchitis. In contrast, the present results suggest that by mixing a composition comprising molecules having a molecular weight in a range 100 to 300 kDa obtained from cells or culture fluid of Bordetella bronchiseptica and a vaccine against trans-mucosal infection such as canine adenovirus type 2 and canine parainfluenza virus, the preventive effects against these trans-mucosal infections can be enhanced, and further, Bordetella bronchiseptica infection itself can be prevented.

EXAMPLE 5

In Example 5, the mucosal adjuvant activity of the composition prepared in Example 1 was evaluated by the transnasal immunotest with guinea pig.

For a test antigen, 5 mg/mL of OVA (ovalbumin; the same hereinafter) dissolved in PBS was used. For an adjuvant, the mucosal adjuvant composition prepared in Example 1 was used.

For a test animal, Hartley guinea pigs (weight: about 300 g) negative to Bordetella hemagglutination inhibition antibody were used. The test guinea pigs were kept in group housing with ad libitum feeding and ad libitum water supply.

OVA (final concentration: 1 mg/mL) and the adjuvant (final concentration: HA value of 64 times) were mixed, and then the mixture was intranasally administered to guinea pigs (n=3) in an amount of 200 μL per animal, followed by an additional administration of the same mixture 14 days after that. Note that in the control group (n=3), the same amount of PBS was administered instead of OVA and the adjuvant. For the adjuvant untreated group (n=3), the mixture in which the same amount of PBS was mixed in place of the adjuvant was administered.

Blood and rectum swab were taken from the test guinea pigs at the initial administration. Further, blood, saliva, rectum swab and dejection were taken from the test guinea pigs on Day 28 (at the termination) after the initial administration. When saliva is taken, 4 mL of a 4 mg/mL-pilocarpine hydrochloride containing solution per animal was intraperitoneally injected as a pretreatment.

The blood withdrawn was inactivated after serum separation and used as a sample. The rectum swab obtained was immersed and well suspended in a 1 mL preservative solution immediately after collection, and used as a sample. The saliva taken was mixed with the same amount of the preservative solution, and used as a sample. The dejection collected was centrifuged after preparing 20% suspension in the preservative solution, and a collected supernatant was used as a sample. Note that a mixture of equal amount of 10% skim milk added PBS and protease inhibitor cocktails (Roche) was used as the preservative solution.

For each sample prepared, an anti OVA antibody titer was measured by the ELISA method (Enzyme-Linked ImmunoSorbent Assay).

A 100 μL solid-phased antigen solution was each dispensed in a 96 well microplate and allowed to stand at 4° C. overnight. The solid-phased antigen solution was prepared by dissolving OVA in PBS to give 10 mg/mL, which was then diluted with 0.05 mol/L carbonate buffer (pH 9.6) to a predetermined concentration for use. When blood serum was used as a sample, the amount of solid-phased antigen was 0.3 μg per well in a 96 well microplate. When rectum swab, saliva and dejection were used as a sample, the amount was 1 μg.

After washing 3 times with PBS-T (0.1% Tween 20 added PBS, the same hereinafter), 100 mL of a stock solution of Block Ace was each dispensed, and allowed to stand for 60 minutes at 37° C. and then blocked. The stock solution Block Ace was prepared by dissolving 4 g Block Ace (DS Pharma biomedical Co., Ltd.) in 100 mL purified water.

After washing 3 times with PBS-T, 100 mL of the prepared sample was each dispensed as a primary antibody into two wells, and allowed to react for 30 minutes.

After washing 3 times with PBS-T, a 100 mL solution of secondary antibody was each dispensed and allowed to react for 30 minutes. For the secondary antibody, peroxidase labeled anti guinea pig IgG sheep antibody (AbD Serotec) or peroxidase labeled anti guinea pig IgA sheep serum (Immunology Consultants Laboratory, Inc.) was used. When serum was used as a sample, this second antibody was diluted 30,000 times with PBS-T for use. When rectum swab or saliva was used as a sample, it was diluted 3,000 times in the same way. When dejection was used as a sample, it was diluted 10,000 times in the same way.

After washing 3 times with PBS-T, a 100 µL substrate solution was each dispensed and allowed to react for 15 to 20 minutes at room temperature or 25° C. Then the reaction was quenched by adding 50 µL of 2M sulfuric acid to measure light absorbance at a wavelength of 450 nm. For a substrate solution, a solution having a composition of 11 mL of 0.1 M sodium acetate (pH 5.5), 110 µL of tetramethylbenzidine (6 mg/mL DMSO) and 110 µL of 3% hydrogen peroxide solution was prepared for use.

After subtracting a reading without a sample (blank) from each measured value for correction, the arithmetic mean was computed for every sample to give an antibody titer.

The results are shown in FIGS. 1 and 2. Table 1 shows the mean value of anti OVA IgG antibody titer within the group, and Table 2 shows the mean value of an anti OVA IgA antibody titer within the group. In the both tables, "serum", "saliva", "rectum swab" and "dejection" represent a type of the samples collected. "At the initial administration" represents the results from the sample collected immediately before the initial administration of the mixture of the antigen and the adjuvant or the comparative control solution thereof. "At the termination" represents the result from the sample collected on Day 28 after the initial administration. In the both tables, "control group" represents the results without administering OVA and the adjuvant. "Adjuvant untreated group" represents the results when only OVA was administered, but not the adjuvant. "Adjuvant treated group" represents the results when OVA and the adjuvant were administered.

TABLE 1

Anti OVA-IgG antibody titers

| | | Control Group | Adjuvant untreated group | Adjuvant treated group |
|---|---|---|---|---|
| Serum | At the initial administration | −0.002 | 0.003 | 0.002 |
| | At the termination | −0.002 | 0.020 | 1.521 |

TABLE 2

Anti OVA-IgA antibody titers

| | | Control Group | Adjuvant untreated group | Adjuvant treated group |
|---|---|---|---|---|
| Saliva | At the termination | −0.007 | 0.004 | 0.678 |
| Rectum swab | At the initial administration | 0.022 | 0.009 | 0.011 |
| | At the termination | −0.001 | 0.002 | 0.595 |

TABLE 2-continued

Anti OVA-IgA antibody titers

| | | Control Group | Adjuvant untreated group | Adjuvant treated group |
|---|---|---|---|---|
| Dejection | At the termination | 0.000 | 0.025 | 1.228 |

As shown in Table 1, for the mean value of anti OVA IgG antibody titers within the group, almost no increase in the antibody titer was observed even at the termination in the control group and the adjuvant untreated group. In contrast, the titer at the termination was 1.521 in the adjuvant treated group, clearly indicating an increase in the antibody titer as compared to a titer of 0.002 at the initial administration.

Further, as shown in Table 2, also for the mean value of the anti OVA IgA antibody titers within the group, almost no increase in the antibody titer was observed in the control group and the adjuvant untreated group whereas in the adjuvant treated group, the anti OVA IgA antibody titer in saliva, in swab at the termination and in dejection was 0.678, 0.595 and 1.228, respectively, clearly indicating an increase in the antibody titer in each of the sample.

These results show that the mucosal adjuvant composition prepared in Example 1 potentiates an immune response against an antigen administered trans-mucosally and enhances antibody inducibility, and i.e., that the composition has a mucosal adjuvant activity.

In Table 1, the anti OVA IgG antibody titer in blood increased by transnasal administration of the mucosal adjuvant composition prepared in Example 1. This result shows that this composition can initiate induction of a systemic immune response.

In Table 2, the anti OVA IgA antibody titers in saliva, rectum swab and dejection were increased by transnasal administration of the mucosal adjuvant composition prepared in Example 1. This result shows that this composition can initiate induction of secretory IgA antibody at different sites of mucous membrane other than the site of administration, such as oral cavity and rectum.

As described above, the results of these Examples herein show that a composition comprising molecules having a molecular weight in a range of 100 to 300 kDa obtained from cells or culture fluid of Bordetella bronchiseptica has an activity to activate mucosal immunity, and also has an immunological enhancement effect at heterotropic mucous membrane and in the whole body.

Figure 1:
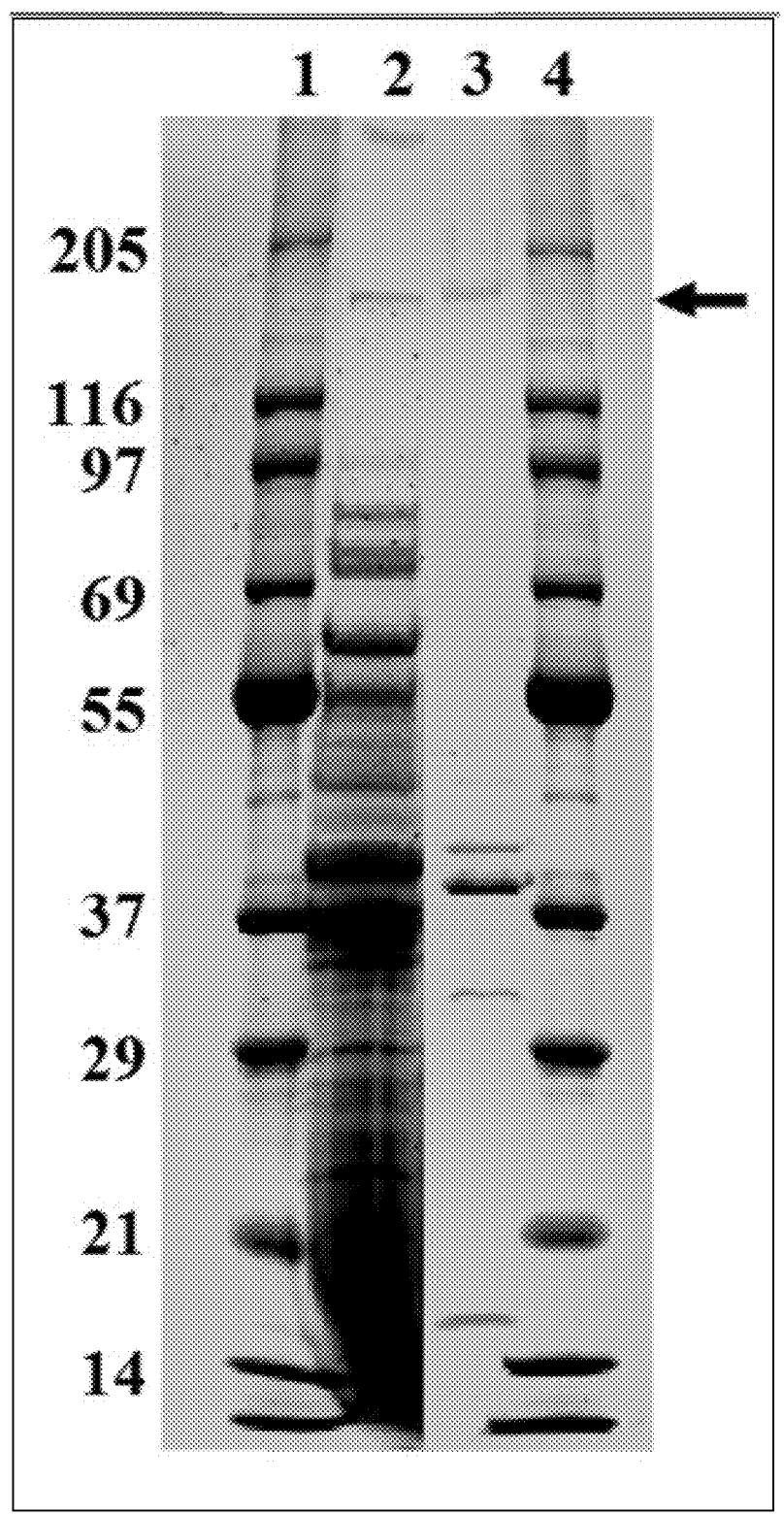
FIG. 1 shows a photograph representing the results from SDS-PAGE of the mucosal adjuvant composition.
Figure 2:
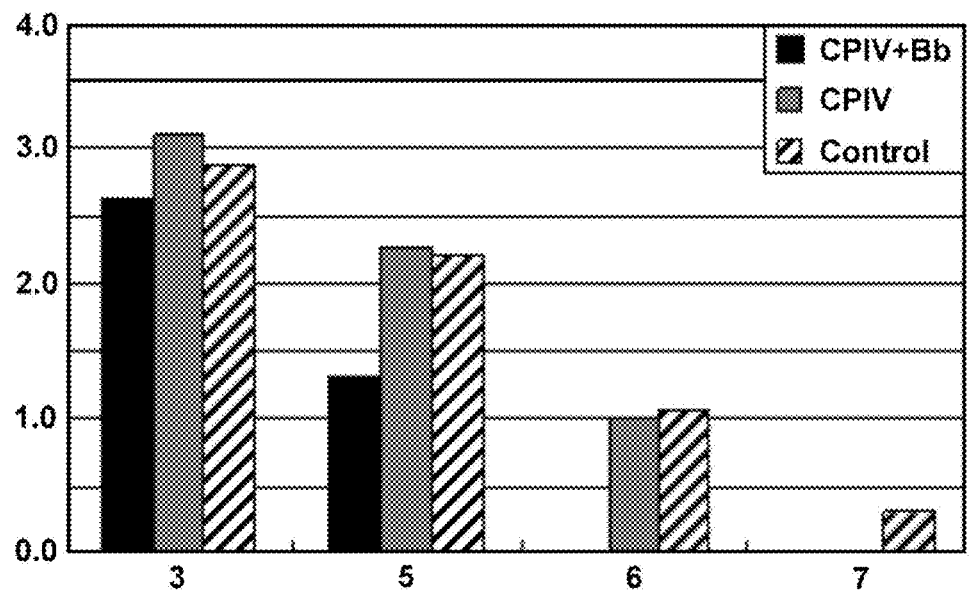
FIG. 2 shows a graph demonstrating immunological enhancement effects against canine parainfluenza virus when the canine parainfluenza virus inactivated vaccine and the adjuvant according to the present invention were administered.
Figure 3:
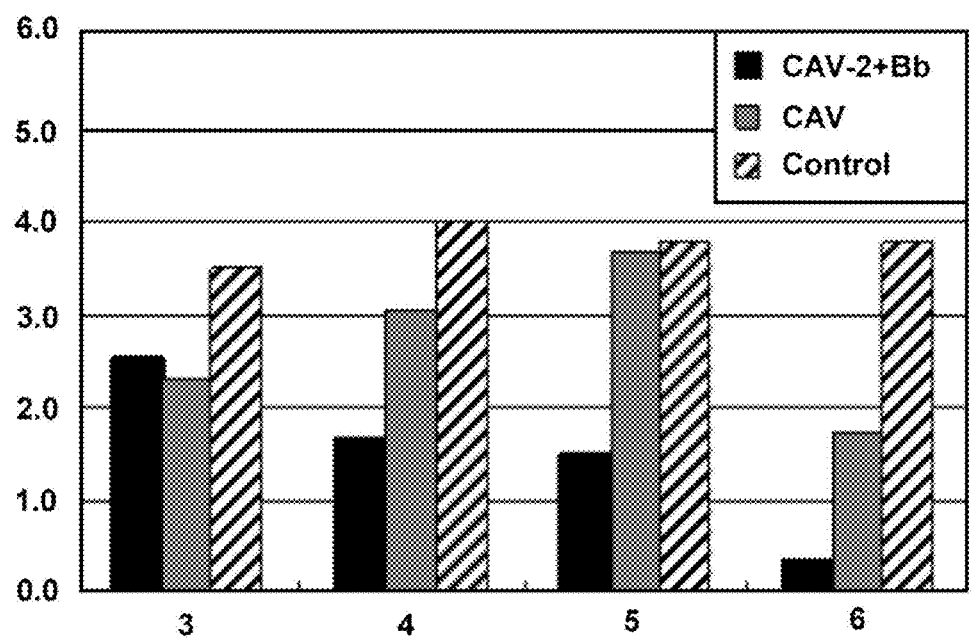
FIG. 3 shows a graph demonstrating immunological enhancement effects against canine adenovirus 2 type infection when the canine adenovirus 2 type inactivated vaccine and the adjuvant according to the present invention were administered.

The invention claimed is:

1. A method of preventing canine infectious tracheobronchitis the method comprising: administering to a subject an effective amount of a vaccine antigen against one or more infections of canine adenovirus and canine parainfluenza virus, and a mucosal adjuvant composition comprising molecules having a molecular weight in a range of 100 to 300 kDa obtained from cells or culture fluid of *Bordetella bronchiseptica*.

2. The method of claim 1 wherein the vaccine antigen and the mucosal adjuvant composition are both administered trans-mucosally.

3. The method of claim 2 wherein said administration induces a systemic immune response against a trans-mucosal infection selected from the group consisting of canine parainfluenza virus, canine adenovirus, canine coronavirus, canine parvovirus, canine distemper virus, canine herpesvirus, reovirus and pneumovirus.

4. The method of claim 3 wherein the vaccine antigen and the adjuvant are administered nasally.

5. The method of claim 2 wherein the vaccine antigen and the mucosal adjuvant composition are both administered transnasally, transtracheally, orally or transurogenitally.

6. The method of claim 2 wherein the vaccine antigen and the adjuvant are administered simultaneously.

7. The method of claim 2 wherein the vaccine antigen and the adjuvant are administered separately.

8. The method of claim 2 wherein at least two separate vaccine antigens derived from two separate pathogens are administered.

* * * * *